United States Patent [19]
Greenway et al.

[11] Patent Number: 6,149,300
[45] Date of Patent: Nov. 21, 2000

[54] INTRAORAL IMAGING SYSTEM

[75] Inventors: Wiliam C. Greenway, Tully; Thomas L. Vogelsong, Jamesville; Andrew W. Beardslee, Liverpool; Michael C. Stone, Skaneateles; David W. Breithaupt, Dewitt; William Bitler, LaFayette, all of N.Y.

[73] Assignee: Welch Allyn, Inc., Skaneateles Falls, N.Y.

[21] Appl. No.: 09/173,501

[22] Filed: Oct. 16, 1998

Related U.S. Application Data

[60] Provisional application No. 60/063,753, Oct. 17, 1997, provisional application No. 60/063,759, Oct. 17, 1997, and provisional application No. 60/063,760, Oct. 17, 1997.

[51] Int. Cl.$^7$ .................................................. G01N 23/04
[52] U.S. Cl. .............................................. 378/191; 378/63
[58] Field of Search .............................. 378/191, 63, 98.5

[56] References Cited

U.S. PATENT DOCUMENTS

| | | | |
|---|---|---|---|
| 5,693,948 | 12/1997 | Sayed et al. | 378/98.8 |
| 5,694,448 | 12/1997 | Morcom | 378/98.8 |

*Primary Examiner*—Craig E. Church
*Attorney, Agent, or Firm*—Wall Marjama & Bilinski

[57] ABSTRACT

An intraoral dental imaging system employs a service unit having a power supply and a light source, and selectively using a video camera having a plug-in module for releasably connecting the video camera to the power supply, or an x-ray camera having a second plug-in module for releasably connecting the x-ray camera to the power supply. In either case the modules have processing means for producing video output signals. These video output signals may be sent to a wide variety of devices connected to the service unit. For instance, they may be used to display an image on a video monitor, such as a CRT, they may be sent to a printer for printing, and they may be sent to a modem for eventual display at another location. In essence, these video output signals may be sent to any device known in the art. Thus, the plug-in modules are highly portable while allowing for interchangeability within the same service unit, thereby allowing a practitioner to use the modules in multiple operatories. In the intraoral x-ray camera the plug-in module may be connected to a sensing head by an umbilical cord. The sensing head includes a first means for converting x-ray input signals into electrical output signals and forwarding those signals to a video processor within the plug-in module, an x-ray sensor means for detecting x-rays, and a triggering means for triggering x-ray acquisition from a sensor, which enables the first means when x-rays are detected and disabling the first means when x-rays are not detected by the sensor means.

27 Claims, 2 Drawing Sheets

INTRAORAL IMAGING SYSTEM

CROSS REFERENCE TO RELATED APPLICATIONS

This is a non-provisional application claiming priority from U.S. Provisional Application Ser. Nos. 60/063,753, 60/063,759 and 60/063,760, all having a filing date of Oct. 17, 1997, which are incorporated herein by reference.

FIELD OF THE INVENTION

The present invention generally relates to medical imaging systems, and deals more particularly with a video and an x-ray imaging system which may easily be employed by dentists in multiple operatories to produce either x-ray images or video images of a patient's oral cavity. This invention further relates to a sensor for automatically turning on and off an intraoral x-ray camera system.

BACKGROUND OF THE INVENTION

Medical imaging systems have long been used by medical professionals, in particular dentists, to view or examine difficult to see areas. The advent of solid state electronics allowed for the development of video based imaging systems. These systems allow the user and the patient to view the interior of a cavity as if they were actually within that cavity.

There have been proposed imaging systems in which x-ray radiation is converted into visible light by using scintillations, and conversion of that light into electronic video signals that are viewed on a display such as a CRT. The electronic video signals are typically derived from a solid state image pickup, such as a CID or CCD, with a lens onto which visible light is focused and then output by the scintillation. Another intraoral imaging system employs a solid state video camera linked to a computer for processing video signals obtained from the camera to show video images on a video display such as a CRT.

Compact imaging systems have not achieved widespread acceptance among, in particular, dentists. A number of drawbacks have contributed to the slow acceptance of these technologies. Current systems require the use of expensive personal computers in order to process the images. Not only are these computers expensive, they are also difficult to use since they are not user friendly in that they are specialized, complex, and difficult to operate. However, even if a doctor or dentist can afford to purchase both systems, space constraints also present a problem since a single office or operatory rarely has the sp ace to accommodate two machines. Another problem with these machines is their general lack of portability. Since each requires a separate service unit, with power supply and lighting, it is difficult to relocate an imaging system from one operatory to another. At the same time, each imaging system has a distinct and inherently different purposes of use. Consequently, in order for dentists to provide optimal care for their patients, a dentist must have quick and easy access to both types of imaging systems.

Accordingly, there is a clear and present need in the art for a simple imaging system which enables the user to interchange x-ray and video imaging modules, thereby allowing the dentist or doctor to quickly and effortlessly interchange between using either video or x-ray imaging within the same operatory. The present invention satisfies this need by addressing and overcoming the problems of the prior art described above.

SUMMARY OF THE INVENTION

The intraoral dental imaging system of the present invention overcomes the disadvantages in the prior art by providing a service unit having a power supply and a light source, and either a video camera having a plug-in module for releasably connecting the video camera to the power supply, or an x-ray camera having a second plug-in module for releasably connecting the x-ray camera to the power supply. In each camera, the modules have processing means for producing video output signals used to display an image on a video monitor. In the intraoral x-ray camera the plug-in module may be connected to a sensing head by an umbilical cord. The sensing head includes a converting means for converting x-ray input signals into electrical output signals and forwarding those signals to a video processor within the plug-in module, an x-ray sensor means for detecting x-rays, and a triggering means for triggering x-ray acquisition from a sensor, which enables the first means when x-rays are detected and disabling the converting means when x-rays are not detected by the sensor means.

Accordingly, it is an object of the present invention to provide an intraoral imaging system capable of using either a video camera or an x-ray camera with solid state imagers for collecting images, and with modules for producing video output signals corresponding to the images.

Yet another object of the present invention to provide an intraoral imaging system capable of using either a video camera or an x-ray camera with solid state imagers for collecting images, and with modules for producing video output signals corresponding to the images for display on a video monitor.

A further object of the present invention is to provide an intraoral imaging system that is easily transportable and interchangeable.

Another object of the present invention is to provide an intraoral imaging system that allows a practitioner to use different plug in modules with different service units located in more than one operatory.

Another object of the present invention is to provide an intraoral imaging system that produces standard video output for display without the use of a computer.

It is yet another object of the present invention to provide a simple, user friendly intraoral imaging system.

A further object of the present invention to provide an intraoral x-ray camera with a means for automatically triggering and ceasing x-ray acquisition from a solid state imager.

Additional objects, advantages, and other novel features of the invention will become apparent to those skilled in the art upon examination of the detailed description and drawings that follow.

BRIEF DESCRIPTION OF THE DRAWINGS

For a better understanding of these and other objects of the invention, reference will be made to the following detailed description of the invention which is to be read in association with the accompanying drawing, wherein.

DETAILED DESCRIPTION OF THE INVENTION

Figure 1:
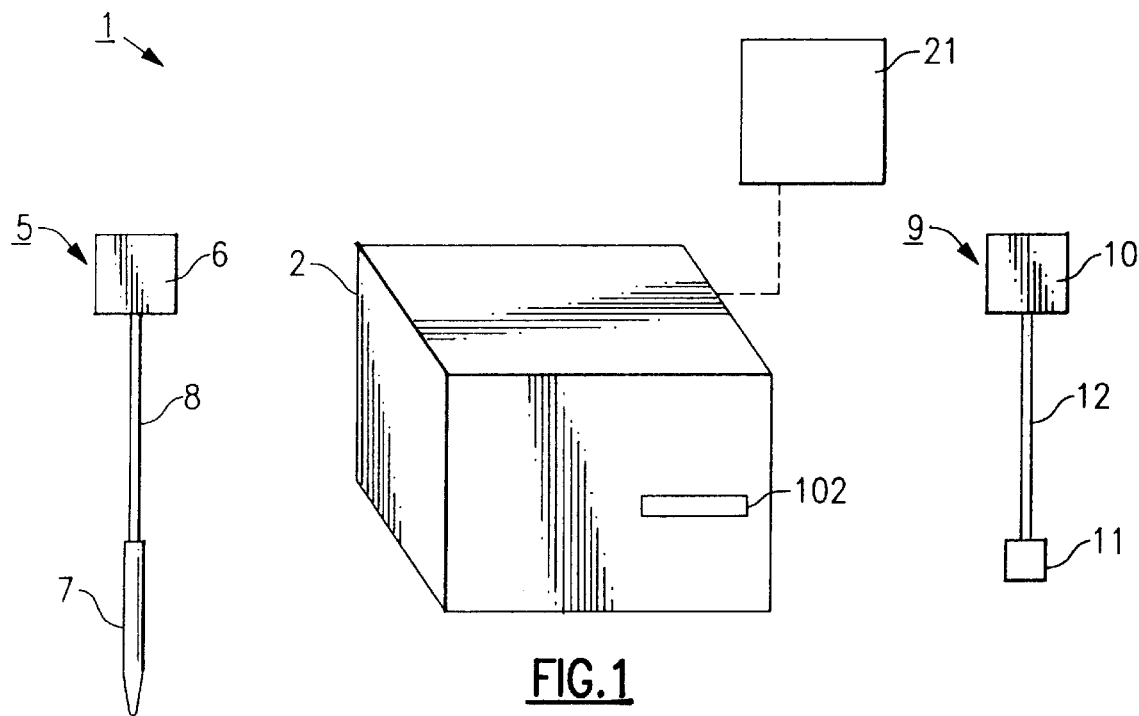
FIG. 1 is a perspective view of an intraoral dental camera system for providing video pictures of targets within an oral cavity.
Figure 2:
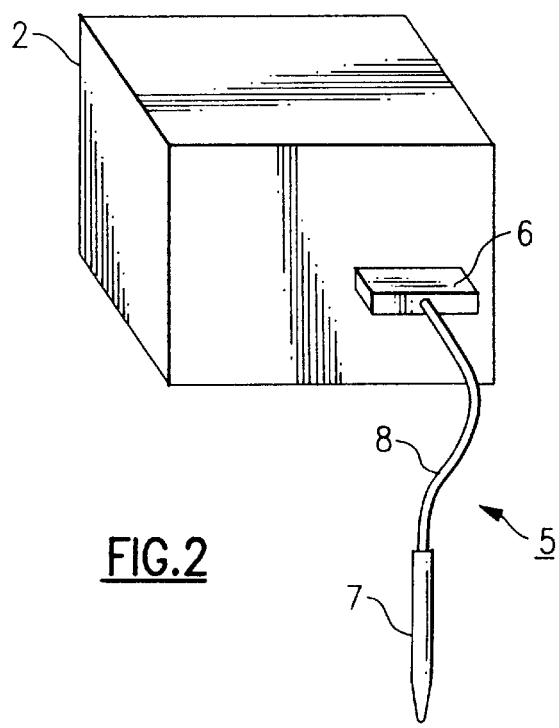
FIG. 2 is a perspective view of a camera suitable for use in the system of FIG. 1 for providing video images of targets within a patient's oral cavity.

FIGS. 1 and 2 show the intraoral dental imaging system 1 of the present invention. The system 1 includes a service unit 2 having a power supply, a light source and video output circuitry. This service unit can accommodate either a video camera 5 or an x-ray camera 9 through a connector port 102. The video camera 5 has a plug-in module 6 for releasably connecting the video camera 5 to the service unit 2. The plug-in module 6 is connected to a probe 7 by a first umbilical cord 8. The plug in module connects to the service unit 2 via the connector port 102. The x-ray camera 9 has a second plug-in module 10 for releasably connecting the x-ray camera 9 to the service unit 2. Similarly, the second plug-in module 10 is connected to a second probe 11 of the x-ray camera 9 by a second umbilical cord 12. The first and second probes are quite different from one another, as the first is used to acquire video images, whereas the second probe is used to acquire x-ray images. As a result, first and second umbilical cords are different in structure. For example, the first umbilical cord employs fiber bundles, whereas a modified coaxial cable will suffice for the second umbilical cord. Each of the modules have processing circuitry for producing video output signals. In the preferred embodiment, the video output signals are displayed as an image on a video display 21. Significantly, both the first 6 and second 10 plug-in modules can be accommodated by and made operational with a singular service unit. For example, a dentist wishing to obtain a view of a patient A's mouth could connect the video camera to the service unit located in a first dental office, and instantaneously a video image of the patients mouth would appear on a video monitor connected to the service unit. Upon discovering an apparent problem with patient A, the dentist could then inspect further by disconnecting the plug-in module of the video camera, and inserting a second plug-in module of the x-ray camera to obtain an x-ray image of the patient A. The dentist could then unplug the x-ray camera, carry it to a second dental office, and plug it into an identical service unit in the second dental office, to obtain an x-ray of a patient B's mouth. Clearly, the practical utility of such modular cameras is invaluable.

Generically, both the video and x-ray cameras include a solid state imager mounted within the probe. This solid state imager is used to receive an image and transform that image into an analog signal. The cameras also include a hybrid circuit mounted adjacent to the solid state imager. This hybrid circuit transmits and receives signals between the appropriate plug-in module and the solid state imager. The solid state imager provides an analog output signal which is sent to a video processor of the hybrid circuit. In addition, a signal processing circuit is included within the plug-in module for receiving and processing the analog signal. An output signal from the signal processing circuit 15 is received by a camera board located within the plug-in module.

In a preferred embodiment, the video camera board receives the analog signal from the signal processing circuit. This video camera board includes a double correlated sampling chip for sampling the analog signal, an A-D converter for converting the analog signal into digital video data, and a digital signal processor for providing both an S video signal and a composite signal to a chip on the camera board. Eventually, this chip buffers the signals, and then outputs the signal to the video display 21.

When the video camera is employed, the first umbilical cord includes a fiber bundle for carrying light from the service unit 2 through the probe 7 into a target region. The solid state imager of the video camera 5 includes lenses for focusing the target image onto a sensor surface of the imager. The images obtained from this target region are relayed through the umbilical cord 8 to the first plug-in module 6, and finally to the service unit 2. These images are real-time, video images. In the preferred embodiment of the video camera, the solid state imaging device is a charge coupled device which transforms the image on its surface into an analog signal which is received and buffered by the hybrid circuit.

By contrast, when the x-ray camera 9 is employed, the recording surface of the solid state imager used in the x-ray camera is covered with a scintillating material for detecting light. This light corresponds to an x-ray image. The images obtained from this target region are relayed through the second umbilical cord 12 to the second plug-in module 10, and finally to the service unit. In the preferred embodiment, the solid state imager is a charge injected device (CID), which transform an image on its surface into an analog signal which is received and buffered by the hybrid circuit. Preferably, this CID has a phosphor coating.

Figure 3:
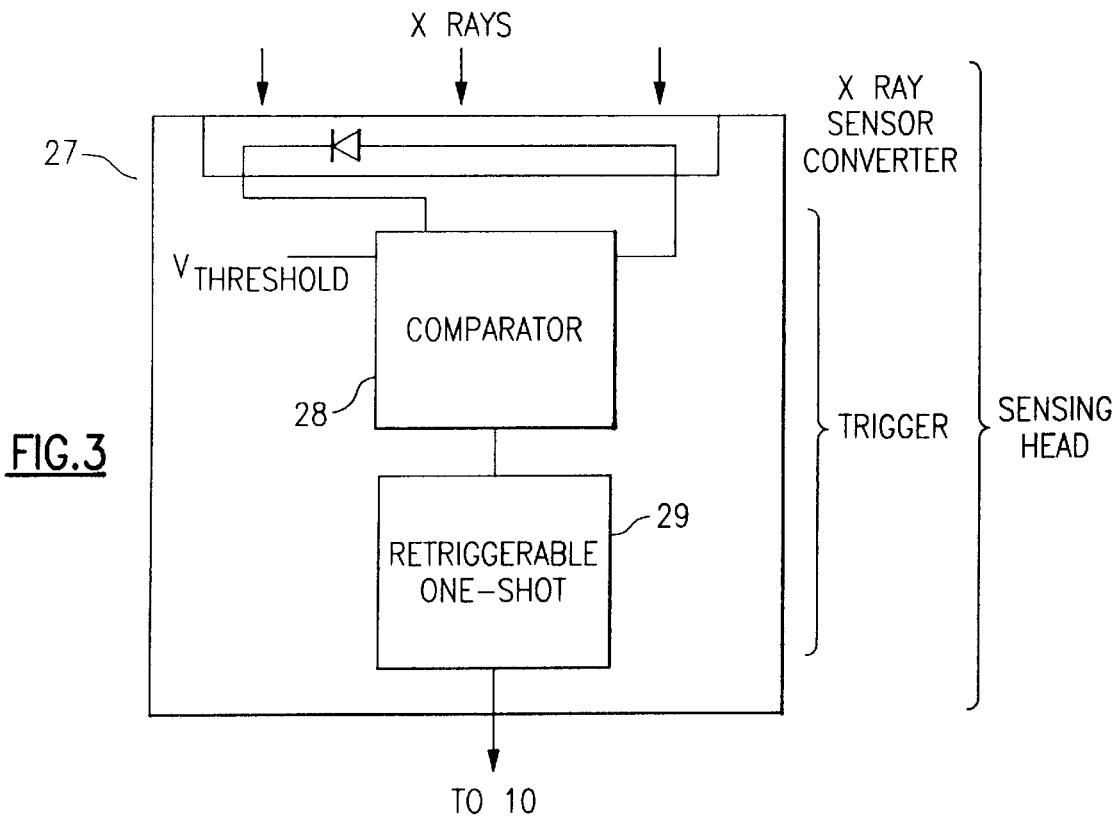
FIG. 3 is a circuit for sensing when the x-ray camera shown in FIG. 2 is receiving x-ray from a source.

Referring to FIGS. 1 and 3, the present invention also provides a unique means of enabling and disabling the x-ray acquisition system described above. A specific embodiment of the intraoral x-ray camera 9 includes a second plug-in module 10 connected to a sensing head by a second umbilical cord 12.

An x-ray sensor in the sensing head detects the x-rays. A converter is provided in the sensing head for converting x-ray input signals into electrical output signals. In the preferred embodiment, the x-ray sensor comprises a plurality of sensors arranged about the periphery of the sensing head. These sensors detect and convert it into an electrical output signal. More specifically, each of the sensors can be photo diodes 27.

A trigger is used for triggering x-ray acquisition from the x-ray sensor means. This trigger enables or "turns on" the converter when x-rays are detected, and disables or "turns off" the converter when x-rays are not detected by the sensor. For example, when the photo diodes 27 output an electrical signal to a comparator 28, this electrical signal causes the threshold voltage of the diode to be exceeded, and the comparator 28 outputs a trigger signal to a retriggerable device 29. By contrast, the comparator 28 will generate an out signal when the time between output pulses exceeds a set limit. This out signal disables the converter, and commences read out of pixels received from a solid state imager. More specifically, the comparator 28 generates a continuous low value output signal during the time of the x-ray, and the comparator 28 generates a high value output signal when the x-ray is terminated. This controls the output of the retriggerable device 29 to produce a video picture of the x-ray image, by forwarding electrical output signals to a video processor mounted in the module 10.

Figure 4:
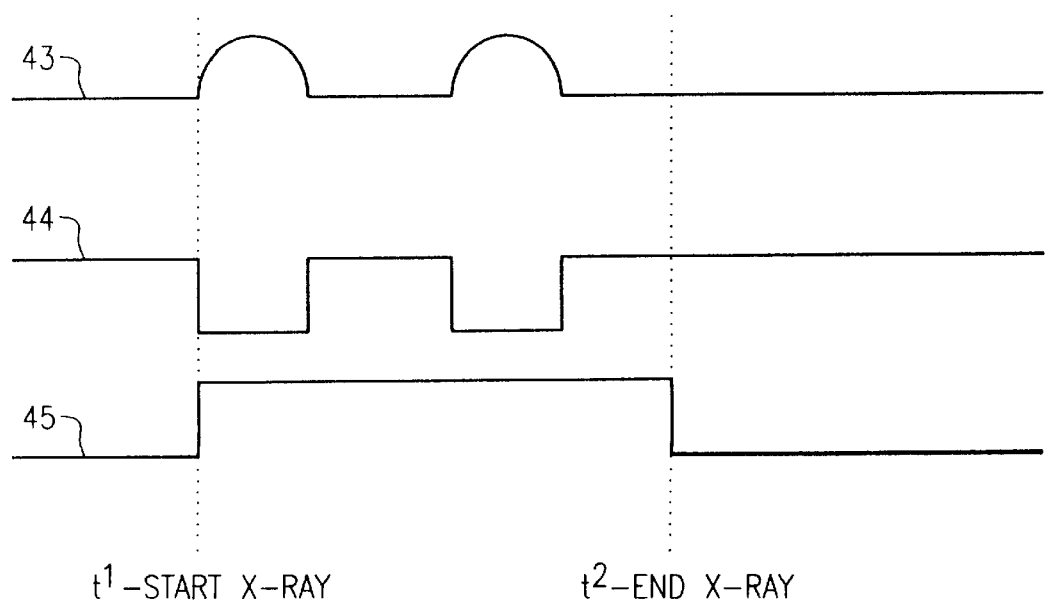
FIG. 4 is a series of electrical waveforms associated with the circuitry shown in FIG. 3.

Referring now to FIG. 4, there are shown a series of waveforms placed upon a timing diagram. Waveform 43 illustrates the output of the x-ray generator or the sensor in response to a pulsed x-ray source at a predetermined frequency. The present system can also handle a continuous pulse of x-ray energy. Waveform 44 is a binary pulse train that is the output of the comparator in response to waveform 43. When the time duration between the output pulses is less than a predetermined value there is indication that the x-ray source is emitting. By the same token, when the time duration between pulses exceeds the predetermined value, there is indication that the x-ray source is not emitting. Waveform 45 is the output of the retriggerable device which goes high when the output pulses of the comparators are at a frequency indicating that the x-ray source is emitting. When the output of the retriggerable device goes high, a signal is applied to the solid state imager telling it to begin to accumulate charge. As is conventional, the recording surface of the solid state imager is covered with a scintillating material. The material is designed to enable the solid state imager to detect light caused by x-ray, thus recording the x-ray image. As noted above, accumulated image data is clocked out of the imager and is sent to the processor of the x-ray camera.

When the time interval between the output pulses of the comparator exceed the predetermined interval or are "out" a signal is generated which commands the video circuitry to commence a read out of the imager pixels.

In the event the x-ray source has continuous emission, the comparator generates a continuous low value output signal during the time of the x-ray and a high value signal when the x-ray signal is terminated. This, in turn, controls the output of the retriggerable device as explained above to produce a video picture of the x-ray image.

While the present invention has been particularly shown and described with reference to the preferred mode as illustrated in the drawings, it will be understood by one skilled in the art that various changes in detail may be effected therein without departing from the spirit and scope of the invention as defined by the claims.

What is claimed is:

1. An intraoral dental imaging system, comprising:
   a processor unit having a power supply, a light source, and video output circuitry;
   a video camera having a first plug-in module for releasably connecting the video camera to said processor unit, said first plug-in module connected to a probe containing a miniature video camera by a first umbilical cord;
   an x-ray camera assembly having a second plug-in module for releasably connecting the x-ray camera assembly to said processor unit, said second plug-in module connected to a second probe containing an x-ray camera by a second umbilical cord,
   each of said first and second plug-in modules having processing means for producing video output signals.

2. The intraoral dental imaging system of claim 1, wherein said video camera assembly and said x-ray camera each include:
   a solid state imager mounted within said probe, said solid state imager having means for receiving an image and transforming said image into an analog signal; and
   a hybrid circuit mounted adjacent to said solid state imager, said hybrid circuit transmitting and receiving signals between a respective plug-in module and said solid state imager, said solid state imager producing an analog output signal which is sent to a video processor of said hybrid circuit.

3. The intraoral dental imaging system of claim 2, further including:
   a signal processing circuit within each of said first and second plug-in modules for receiving and processing said analog signal; and
   a camera board within each module for receiving an output signal from said signal processing circuit.

4. The intraoral dental imaging system of claim 3, including a video display connected to said processing unit wherein said video camera board receives said analog signal from said signal processing board, said video camera board including:
   a double correlated sampling chip for sampling said analog signal;
   an A-D converter for converting said analog signal into digital video data; and
   a digital signal processor for providing both an S video signal and a composite signal to a chip on said camera board which buffers said signals, wherein said signals are then output to said video display.

5. The intraoral dental imaging system of claim 1, further comprising video output means for relaying said video output signals from said processor unit to a video peripheral device.

6. The intraoral dental imaging system of claim 2, wherein a recording surface of said solid state imager of said x-ray camera is covered with a scintillating material for detecting light.

7. The intraoral dental imaging system of claim 6, wherein said solid state imaging device is a charge injected device, said charge injected device transforming said image on its surface into an analog signal which is received and buffered by said hybrid circuit.

8. The intraoral dental camera of claim 2, wherein said images from each of said video camera assembly and said X-ray camera assembly are received in real time when a said assembly is selectively connected to said processor unit.

9. The intraoral dental imaging system of claim 2, wherein said first umbilical cord includes a fiber bundle for carrying light from the processor unit to said probe, said fiber bundle including light transmitting ends for illuminating a target region.

10. The intraoral dental imaging system of claim 2, wherein said video camera assembly includes lenses for focusing said target image onto a sensor surface of the imager.

11. The intraoral dental imaging system of claim 10, wherein said solid state imaging device is a charge couple device, said charge coupled device transforming said image on its surface into an analog signal which is received and buffered by said hybrid circuit.

12. The dental imaging system of claim 1, wherein said x-ray module includes:
   a converting means in the probe for converting x-ray input signals into electrical output signals and forwarding said electrical output signals to a processor mounted in the module;
   an x-ray sensor means in the probe for detecting x-rays; and
   a triggering means for triggering x-ray acquisition, said triggering means associated with said x-ray sensor means for enabling said converting means when x-rays are detected and disabling said converting means when x-rays are not detected by said sensor means.

13. The intraoral x-ray camera of claim 12, wherein said x-ray sensor means comprises a plurality of sensors arranged about the periphery of said probe to pick up said x-ray.

14. The intraoral x-ray camera of claim 13, wherein each of said x-rays sensors is a photo diode for detecting the presence of an x-ray and outputting an electrical signal which is applied to a comparator, said comparator outputting a trigger signal to a retriggerable device when a preset threshold voltage is exceeded.

15. The intraoral x-ray camera of claim 14, wherein said comparator generates a continuous low value output signal during the time of the x-ray, and said comparator generates a high value output signal when the x-ray is terminated, thereby controlling the output of said retriggerable device to produce an x-ray image.

16. The intraoral x-ray camera of claim 15, wherein said comparator, upon exceeding a predetermined time interval between output pulses, generates an out signal commencing read out of pixels received from a solid-state imager.

17. An intraoral dental imaging system, comprising:

a processor unit having a power supply, a light source, and video output circuitry;

a video camera assembly having a first plug-in module for releasably connecting the video camera assembly to said processor unit, said first plug-in module connected to a probe containing a miniature video camera by a first umbilical cord;

an x-ray camera assembly having a second plug-in module for releasably connecting the x-ray camera assembly to said power supply, said x-ray camera assembly including a sensing head connected to a second umbilical cord to a second plug-in module, said second plug-in module being received within said processor unit, converting means in the sensing head for converting x-ray input signals into electrical output signals and forwarding said electrical output signals to a video processor mounted in the second plug-in module, an x-ray sensor means in the sensing head for detecting x-rays, and a triggering means for triggering x-ray acquisition from a sensor, said triggering means associated with said sensor means for enabling said converting means when x-rays are detected and disabling said converting means when x-rays are not detected by said sensor means; and each of said first and second plug-in modules having processing means for producing video output signals.

18. The intraoral x-ray camera of claim 17, wherein said x-ray sensor means comprises a plurality of sensors arranged about the periphery of said sensing head.

19. The intraoral x-ray camera of claim 18, wherein each of said sensors of said X-ray sensor means is a photo diode for detecting the presence of an x-ray and outputting an electrical signal which is applied to a comparator, said comparator outputting a trigger signal to a retriggerable device when a preset threshold voltage is exceeded.

20. The intraoral x-ray camera of claim 19, wherein said comparator generates a continuous low value output signal during the time of the x-ray, and said comparator generates a high value output signal when the x-ray is terminated, thereby controlling the output of said retriggerable device to produce a video picture of the x-ray image.

21. The intraoral x-ray camera of claim 19, wherein said comparator, upon exceeding a predetermined time interval between output pulses, generates an out signal commencing read out of pixels received from an imager.

22. A method for using an intraoral dental imaging system, said system including a processor unit having contained therein a power supply, a light source, and processing circuitry, said system further including a video camera module and an x-ray video module, said method including the steps of:

operably attaching one of said x-ray module and said video camera module to said processor unit;

acquiring one of x-ray images and video images using said attached module; and removing said module from said processor unit; and operably attaching the other of said x-ray module and said video module to said processor unit to acquire corresponding images.

23. The method of claim 22 wherein each of said x-ray module and said video camera module are releasably connectable to said processor unit.

24. The method of claim 22, including the step of processing either of said video images and said x-ray images using the processing circuitry contained in said processor unit.

25. The method of claim 22, including the step of triggering x-ray acquisition using said x-ray module when the presence of x-rays from a source are detected.

26. The method of claim 25, wherein said triggering step includes the step of detecting the presence of an x-ray and outputting an electrical signal to enable acquisition by said x-ray module.

27. The method of claim 24, including the step of displaying one of processed x-ray image and video images on a display substantially in real time.

* * * * *

UNITED STATES PATENT AND TRADEMARK OFFICE
CERTIFICATE OF CORRECTION

PATENT NO. : 6,149,300
DATED : November 21, 2000
INVENTOR(S) : William C. Greenway et al.

It is certified that error appears in the above-identified patent and that said Letters Patent is hereby corrected as shown below:

[75] William C. Greenway, Tully; Thomas L. Vogelsong, Jamesville; Andrew W. Beardslee, Liverpool; Michael C. Stone, Skaneateles; David W. Breithaupt, Dewitt; William Bitler, LaFayette, All of N.Y.

CLAIMS

Claim 1, Column 5, Line 36, after the word camera please insert --assembly--,
Line 37, after the word camera please insert --assembly--,
Line 38, before the word probe please insert --first--, and Claim 2, Column 5, Line 50, after the word camera please insert --assembly--.

Signed and Sealed this

Twenty-ninth Day of May, 2001

*Attest:*

NICHOLAS P. GODICI

*Attesting Officer*  *Acting Director of the United States Patent and Trademark Office*